United States Patent [19]

Williams et al.

[11] 4,233,452

[45] Nov. 11, 1980

[54] DERIVATIVES OF GLYCOLIC AND GLYOXYLIC ACID AS INHIBITORS OF GLYCOLIC ACID OXIDASE

[75] Inventors: Haydn W. R. Williams, Dollard des Ormeaux, Canada; Edward J. Cragoe, Jr., Lansdale; Clarence S. Rooney, Worcester, both of Pa.

[73] Assignee: Merck & Co., Inc., Rahway, N.J.

[21] Appl. No.: 35,753

[22] Filed: May 3, 1979

Related U.S. Application Data

[62] Division of Ser. No. 950,753, Oct. 11, 1978.

[51] Int. Cl.³ .................... C07D 333/24; A61K 31/38
[52] U.S. Cl. ...................................... 549/79; 429/275
[58] Field of Search .................... 260/332.2 H; 549/79

[56] References Cited
PUBLICATIONS

Chem. Abst. vol. 70 (1969) p. 328, 77769k

Primary Examiner—Alan Siegel
Attorney, Agent, or Firm—Michael C. Sudol, Jr.; Harry E. Westlake, Jr.

[57] ABSTRACT

Novel derivatives of glycolic and glyoxylic acid are disclosed which inhibit glycolic acid oxidase and thus are useful in the treatment and prevention of calcium oxalate urolithiasis (calcium oxalate kidney and bladder stone disease).

1 Claim, No Drawings

DERIVATIVES OF GLYCOLIC AND GLYOXYLIC ACID AS INHIBITORS OF GLYCOLIC ACID OXIDASE

This is a division of application Ser. No. 950,753 filed Oct. 11, 1978.

BACKGROUND OF INVENTION

Close to 70% of kidney stones are composed partially or predominantly of calcium oxalate. There is no satisfactory drug specific for the treatment of calcium oxalate urolithiasis, nor for prophylactic use by people prone to recurrent attacks of this disease.

Common procedures for treatment of renal lithiasis due to calcium oxalate consist of surgical removal of stones, or control of the diet to restrict intake of calcium and/or oxalate combined with ingestion of large quantities of water to dilute the urine. Attempts at chemotherapy have included the administration of magnesium oxide, orthophosphate, cellulose phosphate, isocarboxazide, thiazide diuretics, allopurinol and succinimide. Limited success has been realized so far by these drug approaches. No drug which specifically inhibits the biosynthetic formation of oxalic acid is available for the treatment of calcium oxalate renal lithiasis.

The immediate metabolic precursor of the majority of the oxalate in human urine is glyoxylic acid. Much of the glyoxylic acid is in turn derived from glycolic acid. The enzyme glycolate oxidase (GAO) is able to carry out the oxidation of glycolic acid, through glyoxylic acid to oxalic acid. Inhibition of this enzyme will therefore lead to a reduction in the concentration of oxalic acid in the kidney and bladder, reducing the probability that calcium oxalate crystallization will occur. Thus inhibitors of glycolate oxidase provide a specific approach to the prevention and treatment of calcium oxalate lithiasis.

SUMMARY OF THE INVENTION

It has been found that the certain glycolic or glyoxylic acid derivatives are potent inhibitors of the enzyme glycolate oxidase. They are useful in the treatment of calcium oxalate urolithiasis by virtue of their ability to reduce the metabolic generation of urinary oxalic acid. That is these compound diminish or prevent the formation of calcium oxalate kidney and bladder stones.

DETAILED DESCRIPTION

Approximately 70% of all renal calculi contain oxalate as the main anionic component of the matrix. In many, but not all patients, the condition is associated with a higher than normal level of metabolically produced oxalate. The major precursor of oxalate is glyoxylate. Thus, approaches to the reduction of the biosynthetic output of oxalic acid focus on (a.) the prevention of the conversion of glyoxylate to oxalate, and/or (b.) restriction of the production of glyoxylate from its precursors. A major pathway for the biosynthesis of oxalate can be represented as follows:

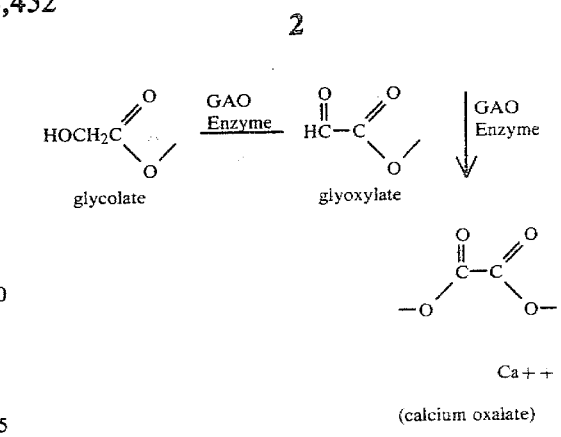

The same enzyme glycolate oxidase participates both in the biosynthesis of glyoxylate and, in its oxidation to oxalate. An inhibitor of the enzyme will act to block at two key points in the chain of reactions contributing to the production of oxalic acid. As a direct consequence of reducing oxalic acid levels in the urine with the compounds of this invention, the formation of oxalate calculi will be reduced or prevented in individuals whose urinary oxalate is primarily of metabolic origin.

The glycolic and glyoxylic acid derivatives described herein are potent inhibitors of glycolate oxidase which are useful in the treatment and prevention of renal disease due to calcium oxalate stone formation in the kidney and bladder. In the genetically inherited diseases termed primary hyperoxaluria types I and II large quantities of oxalic acid are produced metabolically. Crystallization of calcium oxalate, occurring not only in the kidney and bladder but in other tissues as well, frequently results in early death. The compounds of this invention may prove of value in the treatment of these rare, but serious disease states.

The glycolic or glyoxylic acid compounds herein described which are useful in preventing the formation of calcium oxalate kidney or bladder stones can be shown by the following formulae:

$$\underset{\text{R—CHCOOR}_7}{\overset{\overset{\text{OH}}{|}}{}} \qquad \underset{\text{R—C—COOR}_7}{\overset{\overset{\text{O}}{\|}}{}}$$

(Formulae I)

wherein R is selected from the group consisting of

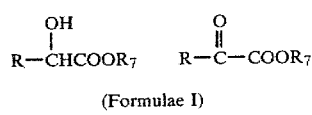 wherein $R_1$ = represents

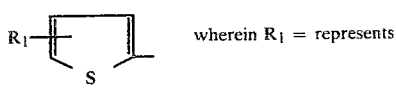

wherein $R_4$ is hydrogen, halo (Cl, Br, F) or loweralkyl ($C_1$–$C_4$),

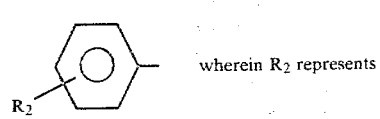 wherein $R_2$ represents

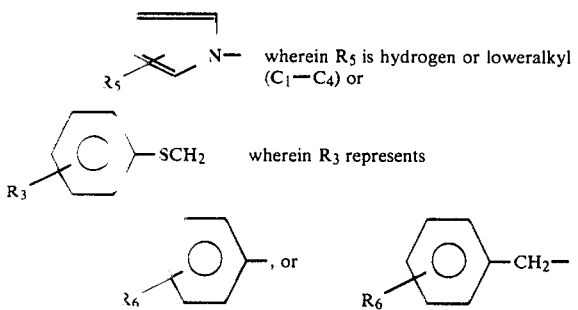 wherein $R_5$ is hydrogen or loweralkyl $(C_1-C_4)$ or wherein $R_3$ represents

, or and wherein $R_6$ is hydrogen, halo, (Cl, Br, F,) or loweralkyl $(C_1-C_4)$; $R_7$ is H, or loweralkyl (straight or branch chained) from 1-6 carbon atoms, or $$N\begin{matrix}R_8\\ \\R_9\end{matrix}$$

where $R_8$ and $R_9$ are $H_7$ or loweralkyl from 1-4 carbon atoms.

Particularly preferred compounds of Formula I are those wherein R represents a substituted thienyl group.

The following compounds

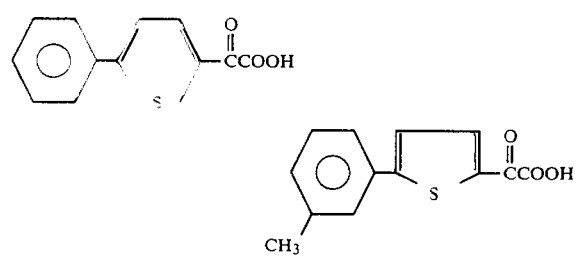

and their ethyl esters are reported in the literature, namely CA 70, 77769k (1969), although their particular use as described in this invention is not known.

The compounds of Formula I wherein R is a (1-pyrrolyl)phenyl substituent and $R_7$ is hydrogen can be prepared from the (1-pyrrolyl)benzaldehyde by first forming the cyanhydrin followed by hydrolysis to a glycolic acid. The pyrrolylbenzaldehydes are obtained by reacting an aminobenzonitrile with a saturated 1,4-dicarbonyl reagent to form the pyrrolyl ring, followed by reduction of the nitrile with Raney Nickel and $NaH_2PO_2$ to the aldehyde. Reaction of the aldehyde with the anion of trimethyl orthothioformate, followed by hydrolysis is an alternative route to the glycolic acid derivatives.

The substituted-2-thienylglyoxylic acids of this invention are prepared by acylation of a 2- or 3-substituted thiophene with ethyl oxalyl chloride under Friedel-Crafts conditions, followed by alkaline hydrolysis of the intermediate ester to the acid. Friedel-Craft reaction of 2-aryl substituted thiophenes results in acylation primarily at the 5-position of the thiophene ring. With 3-substituted thiophenes, acylation takes place at both the 2- and 5-positions, necessitating separation of the isomeric products by column chromatography. With 2-benzylthiophene, acylation occurs at both the 2- and the 5-positions, necessitating chromatographic separation of the products.

The substituted-2-thienylglyoxylic acids on reduction with sodium borohydride are converted to the corresponding substituted-2-thienylglycolic acid derivatives.

An alternative procedure for the thiopheneglycolic acid derivatives of this invention involves starting from the appropriate substituted thiophene-2-carboxaldehyde and reacting with the anion of trimethyl orthothioformate (followed by hydrolysis) as described above for the pyrrolyl substituted phenylglycolic acids.

The starting 2- (or 3-)-substituted thiophenes are known compounds, or are prepared by standard procedures well known in the art.

Finally, the preparation of the 3-(4-biphenylylthio)-2-hydroxypropionic acids are accomplished by alkylation of a 4-biphenylylthiol with ethyl 3-bromopyruvate, followed by reduction of the ketone group with sodium borohydride and then hydrolysis of the ester to the acid.

Ester derivatives of this invention, when not obtained as intermediates in the synthesis of the corresponding acids, are readily prepared from the acids by standard methods well known in the art. These include esterification using a mixture of hydrogen chloride and alcohol, or by reaction of the acid with the appropriate diazoalkane. The amide derivatives of this invention are prepared by heating the appropriate ester intermediate with the desired amine in a solvent such as ethanol, isopropanol, toluene or the like; or by reaction of the amine with an acid chloride intermediate prepared by reacting the acid with thionyl or oxalyl chloride.

Included within the scope of the invention are the pharmaceutically acceptable salts of the glycolic or glyoxylic acids. Thus salts are readily formed by reacting the glycolic or glyoxylic acids with the usual inorganic cations such as sodium, potassium and ammonium. Salts with organic amines such as trimethylamine, triethylamine, n-butylamine and the like are also very stable. The neutralization can be carried out by a variety of procedures known to the art to be generally useful for the preparation of such salts. The choice of the most suitable procedure will depend on a variety of factors including convenience of operation, economic considerations, and particularly the solubility characteristics of the particular free base, the acid, and the acid addition salt.

The glycolic or glyoxylic acids and their ester and amide derivatives of Formula I can be administered to patients (both human and animal) having, or being prone, to calcium oxalate kidney or bladder stone disease by formulating them in a composition such as tablet, capsule or elixir for oral administration. Sterile solutions or suspensions can be used for parenteral administration. About 25 to 500 mg of the glyoxylic or glycolic acid derivatives or a pharmaceutically acceptable salt is compounded with a pharmaceutically acceptable vehicle, carrier, excipient, binder, preservative, stabilizer, flavor, etc., in a unit dosage form as called for by accepted pharmaceutical practice. The amount of active substance in the composition is such that dosage in the range indicated is obtained. The total daily dose administered to patients having or prone to calcium oxalate kidney or bladder stone disease will be in the 50 mg to 2000 mg range with a preferred daily dose being 100 mg to 1000 mg of active ingredient. It will be realized by those skilled in the art that the dosage range for any particular patient (animal or human) will depend upon the severity of the disease treated, weight of the patient and any other condition which the physician or other person skilled in the art will take account of.

Illustrative of the adjuvants which may be incorporated in tablets, capsules and the like are the following: a binder such as gum tragacanth, acacia, corn starch or gelatin; an excipient such as dicalcium phosphate; a disintegrating agent such as corn starch, potato starch, alginic acid and the like; a lubricant such as magnesium stearate; a sweetening agent such as sucrose, lactose, or saccharin; a flavoring agent such as peppermint, oil of wintergreen or cherry. When the dosage unit form is a capsule, it may contain in addition to materials of the above type a liquid carrier such as a fatty oil. Various other materials may be present as coatings or to otherwise enchance the pharmaceutical elegance of the preparation. For instance, tablets may be coated with shellac, sugar or the like. A syrup or elixir may contain the active compound, sucrose as a sweetening agent, methyl and propyl parabens as preservatives, a dye and a flavoring such as cherry or orange flavor.

Sterile compositions for injection can be formulated according to conventional pharmaceutical practice by dissolving or suspending the active substance in a conventional vehicle such as water for injection, a naturally occurring vegetable oil like sesame oil, coconut oil, peanut oil, cottonseed oil, etc., or a synthetic fatty vehicle like ethyl oleate or the like. Buffers, preservatives, antioxidants and the like can be incorporated as required.

Following are examples which illustrate the preparation of several compounds and compositions falling within our invention. They should be construed as illustrations of our invention and not limitations thereof.

EXAMPLE 1

5-Benzylthien-2-ylglyoxylic Acid (Potassium Salt)

To a stirred mixture of 2-benzylthiophene (17.4 g, 0.1 mole) and ethyl oxalyl chloride (13.6 g, 0.1 mole) in benzene (200 ml) cooled in an ice bath, was added titanium tetrachloride (18.9 g, 0.1 mole) in benzene (50 ml). The mixture was stirred for 3 hrs. at 27° C. and then thoroughly mixed with ice-water (50 ml). Extraction with methylene chloride, followed by chromatography on silica gel (1.8 kg, elution with carbon tetrachloride-1,1,1-trichloroethane (65:35) gave an oil which on further purification by short-path distillation (b.p. 115° C., 0.4 Torr) provided 4.6 g of ethyl 5-benzylthien-2-ylglyoxylate.

When 2-propyl oxalyl chloride, n-butyl oxalyl chloride, or n-hexyl oxalyl chloride are used in the above reaction, the corresponding 2-propyl, n-butyl and n-hexyl 5-benzylthien-2-ylglyoxylates are obtained.

A mixture of the 5-benzylthien-2-ylglyoxylate (1.37 g, 0.005 mole), potassium hydroxide (0.66 g, 0.01 mole), dioxane (3.3 ml), ethanol (33 ml) and H$_2$O (6.6 ml) was stirred 3 hrs. at 27° C. The reaction mixture was concentrated and chilled to induce crystallization of 0.9 g of the potassium salt of 5-benzylthien-2-ylglyoxylic acid.

Analysis for C$_{13}$H$_9$KO$_3$S: Calc.: C, 54.91; H, 3.19; S, 11.27; Found: C, 54.83; H, 3.44; S, 11.35.

EXAMPLE 2

5-(4-Chlorophenyl)thien-2-ylglyoxylic Acid (potassium Salt)

When the above procedure was carried out starting with 2-(4-chlorophenyl)thiophene the potassium salt of 5-(4-chlorophenyl)thien-2-ylglyoxylic acid was obtained, m.p. 339°–43° C.

Analysis for C$_{12}$H$_6$ClKO$_3$S; Calc.: C, 47.30; H, 1.99; Cl, 11.64; S, 10.52; Found: C, 47.15; H, 2.26; Cl, 11.67; S, 10.41.

EXAMPLE 3

5-Benzylthien-2-ylglycolic Acid

To a solution of the potassium salt of 5-benzylthien-2-ylglyoxylate (0.71 g, 0.0025 mole) in methanol (10 ml) and H$_2$O (2 ml) was added sodium borohydride (0.1 g) with stirring. After 3 hours the reaction mixture was diluted with H$_2$O (20 ml), the pH adjusted to 1-2 with 6 N HCl, and the solution extracted with methylene chloride. The residue, obtained on evaporation of the extract, on recrystallization from carbon tetrachloride-1,1,1-trichloroethane (2:1) gave 0.5 g (81%) of 5-benzylthien-2-ylglycolic acid, m.p. 81°–82° C.

Analysis for C$_{13}$H$_{12}$O$_3$S; Calc.: C, 62.89; H, 4.87; S, 12.91; Found: C, 62.43; H, 5.09; S, 12.84.

EXAMPLE 4

5-(4-Chlorophenyl)thien-2-ylglycolic Acid

When the above procedure was repeated starting with the potassium salt of 5-(4-chlorophenyl)thien-2-ylglyoxylic acid, there was obtained 5-(4-chlorophenyl)thien-2-ylglycolic acid, m.p. 158°–160° C.

Analysis for C$_{12}$H$_9$ClO$_3$S: Calc.: C, 53.63; H, 3.37; S, 11.90; Found: C, 53.70; H, 3.44; S, 12.03.

EXAMPLE 5

Synthesis of 4-(1-pyrrolyl)phenylglycolic Acid

A mixture of 4-aminobenzonitrile (50 g., 0.42 mole), 2,5-dimethoxytetrahydrofuran (56 g., 0.42 mole) and 4 A molecular sieves (184 g) in toluene (560 ml) was heated under reflux for 24 hrs. The residue from evaporation was washed with pet. ether and then recrystallized from diisopropyl ether to yield 42.5 g (60%) of 4-(1-pyrrolyl)-benzonitrile, m.p. 104°–106° C.

To a stirred mixture of 4-(1-pyrrolyl)-benzonitrile (7.5 g, 0.45 mole) and NaH$_2$PO$_2$ (15 g., 0.17 mole) in pyridine (108.5 ml) was added moist Raney nickel (5 g). After stirring for 1.5 hrs. at 40°–45° C., the catalyst was removed by filtration. After washing the separated catalyst with H$_2$O followed by ethyl acetate, the combined filtrate was diluted further with H$_2$O and extracted with ethyl acetate. Dilution of the concentrated extract with H$_2$O gave 6.5 g (85%) of 4-(1-pyrrolyl)benzaldehyde, m.p. 92°–95° C.

A solution of n-butyllithium in hexane (9.2 ml, 2.3 molar) was added dropwise to a stirred solution of trimethyl orthothioformate (3.24 g, 0.021 mole) in dry tetrahydrofuran (25 ml) at −78° C. After stirring at −78° C. for 0.75 hr., a solution of 4-(1-pyrrolyl)benzaldehyde (3.4 g., 0.02 mole) in tetrahydrofuran (25 ml) was added dropwise. Stirring at −78° C. was continued for 2 hr. Acetic acid (1.2 ml) was added and the reaction mixture diluted with H$_2$O (200 ml), and extracted with methylene chloride (2×35 ml). The combined extracts were washed with H$_2$O, dried (Na$_2$SO$_4$) and evaporated. The residue was recrystallized from isopropanol to give 2-hydroxy-2-[4-(1-pyrrolyl)phenyl]-1,1,1-tris-methylthioethane (4.5 g, 69%), m.p. 101°–103° C.

A mixture of 2-hydroxy-2-[4-(1-pyrrolyl)-phenyl]-1,1,1-tris-methylthioethane (3.25 g, 0.01 mole) HgO (0.65 g, 0.03 mole) and HgCl$_2$ (8.15 g, 0.03 mole) in ethanol (250 ml) was heated at reflux under nitrogen for 24 hr. The reaction mixture was filtered and the solids washed with methylene chloride. The filtrate was evaporated. The residue, dissolved in methylene chloride (300 ml), was washed with H₂O (2×50 ml), 4 M aqueous NH₄Cl (2×50 ml) and brine (2×20 ml). After drying (MgSO₄), evaporation afforded a beige solid (2.6 g) which on recrystallization from isopropanol gave 1.64 g (67%) of ethyl 4-(1-pyrrolyl)-phenylglycolate, m.p. 126.5°-128.5° C.

A mixture of ethyl 4-(1-pyrrolyl)phenylglycolate (0.49 g., 0.002 mole), ethanol (10 ml), dioxane (1.2 ml) and 2 M aqueous KOH (1.5 ml) was stirred at 27° C. for 3 hrs., and then evaporated to dryness. The residue was dissolved in H₂O. The solution was acidified with acetic acid and extracted with ethyl acetate (3×15 ml). The combined extracts after washing with H₂O and drying (MgSO₄), evaporation and recrystallization of the residue from H₂O gave 0.19 g (44%) of 4-(1-pyrrolyl)-phenylglycolic acid, m.p. 168°-168.5° C.

Analysis for $C_{12}H_{11}NO_3$; Calc.: C, 66.35; H, 5.10; N, 6.45; Found: C, 66.35; H, 5.27; N, 6.32.

When the above procedure is carried out using 2,5-hexanedione in place of 2,5-dimethoxytetrahydrofuran, the corresponding 4-(2,5-dimethylpyrrol-1-yl)phenylglycolic acid is obtained.

EXAMPLE 6

3-(4-Biphenylthio)-2-hydroxypropionic Acid

To a solution of 4-biphenylthiol (2.79 g., 0.015 mole) in dry tetrahydrofuran (30 ml) and dimethylformamide (6 ml) was added portionwise sodium hydride (0.37 g., 0.015 mole) with stirring under a nitrogen atmosphere. The resulting solution was added dropwise over 45 min. to ethyl bromopyruvate (3.0 g, 0.015 mole) in dry tetrahydrofuran (30 ml) with stirring under nitrogen at −7° to −10° C. After 1 hr. at 25° C. ice-water (250 ml) was added. Extraction with methylene chloride (3×50 ml) followed by evaporation of the extract, and recrystallization of the residue from carbon tetrachloride gave 1.56 g (35%) of ethyl 3-(4-biphenylylthio)-2-oxopropionate, m.p. 154.5°-156° C.

When the above procedure is repeated using 2-propyl bromopyruvate, n-butyl bromopyruvate or n-hexyl bromopyruvate in place of ethyl bromopyruvate, there is obtained the corresponding 2-propyl, n-butyl or n-hexyl 3-(4-biphenylthio)-2-oxopropionate derivatives.

To a stirred suspension of ethyl 3-(4-biphenylylthio)-2-oxopropionate (1.44 g, 0.0048 mole) in isopropanol (24 ml) was added sodium borohydride (0.18 g, 0.0048 mole). After 2 hrs., water (75 ml) and 2 N HCl (0.5 ml) were added. The mixture was extracted with methylene chloride (2×150 ml). The contents of the combined extracts, after drying (Na₂SO₄) and concentration, were chromatographed on silica gel (120 g) using 1,1,1-trichloroethane as eluting solvent to obtain 0.35 g (24%) of ethyl 3-(4-biphenylylthio)lactate, m.p. 101.5°-102° C.

A mixture of ethyl 3-(4-biphenylylthio)lactate (0.093 g, 0.31 mmole), in NaOH (0.5 ml), water (2 ml) and tetrahydrofuran (1 ml) was stirred overnight at 25° C. The mixture was acidified (1 N HCl, 0.5 ml) and then extracted with methylene chloride (3×5 ml). The residue from evaporation of the methylene chloride was recrystallized from acetonitrile to yield 0.065 g of 3-(4-biphenylylthio)-2-hydroxypropionic acid, m.p. 175.5°-176° C.

Analysis for $C_{15}H_{14}O_3S$: Calc.: C, 65.67; H, 5.14; S, 11.64; Found: C, 65.64; H, 5.09; S, 11.82.

When the above procedure is carried out starting from 4'-chlorobiphenyl-4-thiol there is obtained 3-(4'-chlorobiphenylthio)-2-hydroxypropionic acid.

EXAMPLE 7

5-Benzyl-2-thienylglyoxylic Acid Amide

A mixture of 5-benzyl-2-thienylglyoxylic acid potassium salt (5.7 g, 0.02 mole), thionyl chloride (3.6 g, 0.03 mole) and toluene (25 ml) is heated at reflux for 2 hours. The solvent and excess thionyl chloride are removed under vacuum. To the residue is added tetrahydrofuran (100 ml) saturated with ammonia gas at 0° C. Ammonia is bubbled through at 0° C. for 30 minutes and the mixture allowed to stand at room temperature overnight. After evaporation of the solvent, the residue is partitioned between chloroform and water. The chloroform phase after drying and evaporation affords the title compound.

When the above procedure is repeated using 5-(4-chlorophenyl)-2-thienylglyoxylic acid potassium salt, there is obtained 5-(4-chlorophenyl)-2-thienylglyoxylic acid amide.

To prepare the corresponding N-mono- or disubstituted amide derivatives, the ammonia in the above procedure should be replaced by the appropriate substituted amine. For example to prepare the corresponding N-methylamide derivatives N-methylamine should be substituted for the ammonia in the above procedure. Where the substituted amine is a liquid, rather than a gas at room temperature, (e.g. n-butylamine), an excess of the amine may be added initially to the tetrahydrofuran solvent in place of ammonia.

EXAMPLE 8

5-Benzyl-2-thienylglycolic Acid Ethyl Ester

A mixture of 5-benzyl-2-thienylglycolic acid potassium salt (5.7 g, 0.02 mole) and absolute ethanol (50 ml) containing 2 g of hydrogen chloride gas is heated at reflux for 5 hours. The solvent is evaporated under vacuum and the residue partitioned between chloroform and water. The chloroform solution is washed with saturated sodium bicarbonate solution, water, and dried over MgSO₄. On evaporation the title ester is obtained.

When the above procedure is carried out starting with 5-(4-chlorophenyl)thien-2-ylglycolic acid, there is obtained 5-(4-chlorophenyl)-thien-2-ylglycolic acid ethyl ester.

For the preparation of other alkyl esters, the appropriate alcohol is substituted for ethanol in the above procedure.

EXAMPLE 9

Dry-filled capsules containing 50 mg of active ingredient per capsule

|  | Per Capsule |
| --- | --- |
| 5-Benzylthien-2-ylglycolic Acid | 50 mg |
| Lactose | 149 mg |
| Magnesium Stearate | 1 mg |
| Capsule (Size No. 1) | 200 mg. |

The 5-benzylthien-2-ylglycolic acid is reduced to a No. 60 powder and then lactose and magnesium stearate are passed through a No. 60 bolting cloth onto the powder and the combined ingredients admixed for 10 minutes and then filled into a No. 1 dry gelatin capsule.

What is claimed is:

1. 5-Benzylthien-2-ylglyoxylic acid.

* * * * *